(12) United States Patent
Miyazawa et al.

(10) Patent No.: US 6,448,202 B1
(45) Date of Patent: Sep. 10, 2002

(54) WITHERING-PREVENTING AND QUICK-ACTING NUTRITION SUPPLEMENTING AGENT FOR GRAMINEOUS PLANTS

(75) Inventors: Yuki Miyazawa; Masahiko Kurauchi, both of Kawasaki; Makoto Takeuchi, Tokyo; Hiroyuki Sato, Kawasaki, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/695,993

(22) Filed: Oct. 26, 2000

(30) Foreign Application Priority Data

Oct. 29, 1999 (JP) ............................................ 11-308281

(51) Int. Cl.⁷ ........................ A01N 43/36; A01N 43/90
(52) U.S. Cl. ...................................... 504/136; 504/287
(58) Field of Search ................................. 504/287, 136

(56) References Cited

U.S. PATENT DOCUMENTS

| | | | | |
|---|---|---|---|---|
| 4,520,103 A | * | 5/1985 | Ensley, Jr. ................... | 435/121 |
| 5,243,094 A | * | 9/1993 | Borg ........................... | 568/822 |
| 5,288,852 A | * | 2/1994 | Yamada et al. .............. | 530/351 |
| 5,780,709 A | | 7/1998 | Adams et al. .............. | 800/205 |
| 6,143,695 A | | 11/2000 | Murayama .................. | 504/241 |

FOREIGN PATENT DOCUMENTS

| | | | |
|---|---|---|---|
| EP | 0 656 421 | * | 6/1995 |
| EP | 0 841 007 | | 5/1998 |
| JP | 63 045211 | | 2/1988 |
| JP | 10 279405 | | 10/1998 |
| JP | 10-279405 | * | 10/1998 |
| WO | WO 91/10726 | | 7/1991 |

\* cited by examiner

*Primary Examiner*—S. Mark Clardy
(74) *Attorney, Agent, or Firm*—Oblon, Spivak, McClelland, Maier & Neustadt, P.C.

(57) ABSTRACT

Herein is disclosed a withering-preventing and quick-acting nutrition supplementing agent for a gramineous or the like plant such as a lawn grass or the like which agent comprises, as the effective ingredient (s), proline alone or both proline and inosine concurrently, according to which a withering preventing and quick-acting nutrition supplementing agent which is not a chemical fertilizer and does not adversely affect environment and humans and animals, as well as a method for applying the same, can be provided.

25 Claims, 1 Drawing Sheet

WITHERING-PREVENTING AND QUICK-ACTING NUTRITION SUPPLEMENTING AGENT FOR GRAMINEOUS PLANTS

BACKGROUND OF THE INVENTION

1. Technical Field to which the Invention Belongs

The present invention relates to a withering-preventing and quick-acting nutrition supplementing agent for a plant such as a gramineous plant, more particularly to a withering-preventing and quick-acting nutrition supplementing agent for a plant such as a gramineous plant which agent comprises proline which is effective for, e.g., a lawn grass going to wither and die by a stress caused by temperature or pruning or leaf rot disease.

2. Prior Art

Hitherto, some examples have been known where an amino acid-related compound, e.g., proline is applied to a plant.

For example, (a) Japanese Patent Application Laid-open (Kokai) No. 67051/1973 discloses a fruiting and fruit-enlarging promoting agent containing at least one nucleoside or nucleotide and proline.

In respect to this fruiting and fruit-enlarging promoting agent, however, the target plants are entirely different from those plants to be applied with the withering-preventing and quick-acting nutrition supplementing agent for a gramineous plant such as a lawn grass according to the present invention, and the promoting agent necessitates concurrent use of a nucleoside or a nucleotide in combination with proline. In addition, the application method comprises performing foliar application (e.g., spraying or spreading the promoting agent onto the leaves) at intervals of one week by injecting dropwise the fruiting and fruit-enlarging promoting agent (concentration of 40 ppm) through a syringe for two months, and therefore, is obviously different from that of the present invention.

(b) Japanese Patent Application Laid-open (Kokai) No. 279405/1998 discloses a method for controlling pine tree-withering wherein a plant activating substance containing proline as the main ingredient and an alkaline ion water are sprayed to the above-ground parts of a pine tree and/or such a plant activating substance and an acidic ion water are fed to the subterranean parts of a pine tree.

However, this method for controlling pine tree withering is entirely different in target plants from the method for withering-prevention and quick-acting nutrition supplementation for a gramineous plant such as a lawn grass according to the present invention. In addition, according to the prior art method, a solution having a proline concentration of 30 to 300 ppm is applied and therefore, the application method is obviously different from that of the withering-preventing and quick-acting nutrition supplementing agent for a gramineous plant such as a lawn grass according to the present invention.

For example, lawns are utilized in many places such as parks, gardens and ball game fields, and are indispensable for golf courses or golf links. However, a large quantity of fertilizer and agricultural chemical is hitherto used for maintenance of lawn grass and the use has become a big problem in view of environmental aspect. For example, synthetic fungicides (agricultural chemicals) have hitherto been applied for controlling leaf rot disease of lawn grass, but there is a possibility that the application exerts undesirable influences on the natural environment.

Furthermore, a lawn grass, especially cold-district type grass, suffers indirectly growth stop and directly withering due to a stress caused by high temperatures, but there is only a measure of good air-ventilation against the problems.

As for gramineous plants such as a lawn grass, it is known to fertilize amino acids as the nitrogen source, but the amino acids are generally used in the form of a multi-component fertilizer such as a hydrolysate of plants or animals or a fermentation waste liquid, their components being indistinct. It is required to reduce fertilization in view of the problems of accumulation of minerals in the soil and so on, so that there is a demand for a quick-acting fertilizer (quick-acting nutrition supplementing agent) which can supply effectively a necessary amount of nitrogen. For this purpose, urea preparations for foliar application are frequently used, but the urea tends to accumulate in the soil and may cause phenomena such as leaf scorch and the like in some cases depending on the concentration. Accordingly, it has been required to develop a withering-preventing and quick-acting nutrition supplementing agent which can substitute for it.

SUMMARY OF THE INVENTION

[Problems to be Solved by the Invention]

It is an object of the present invention to provide a withering-preventing and quick-acting nutrition supplementing agent which is not a chemical fertilizer and does not adversely affect environment and humans and animals, as well as a method for applying the same. Other objects will become apparent during the following description.

[Means for Solving the Problems]

As a result of extensive studies for achieving the aforementioned objects, the present inventors have first found that amino acids, especially proline, serine and the like exhibit a remarkable effect on prevention of withering of a gramineous plant, and that the effect is especially enhanced by combination with inosine among various nucleosides, and accomplished the present invention based on these findings.

Namely, the present invention relates to a withering-preventing and quick-acting nutrition supplementing agent for a plant such as a gramineous plant which agent comprises proline as the effective ingredient, and a method for withering prevention and quick-acting nutrient supplementation of a plant such as a gramineous plant which method comprises applying said withering-preventing and quick-acting nutrition supplementing agent to the soil or hydroponic water, or performing foliar application of said agent.

DETAILED DESCRIPTION OF THE INVENTION

Figure 1:
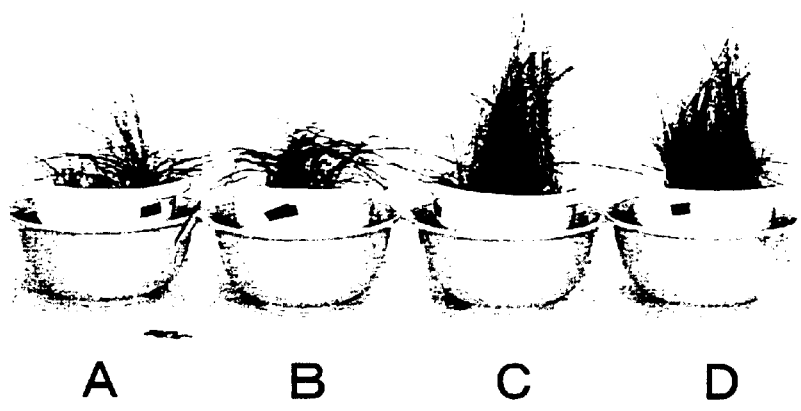
FIG. 1 shows the state of the pot cultivation of the lawn grass plants on the 35th day from the transplantation (Example 1).

The following will explain the present invention in detail.

Gramineous plants, especially lawn grasses, rice plants, and pasture plants are included in the target plants to which the withering-preventing and quick-acting nutrition supplementing agent of the present invention is applied, and the agent is particularly effective to lawn grasses among them.

Proline is not necessarily required to be a purified product, and can be a hydrolysate of a protein or a mixture of amino acids containing a large quantity of proline unless it exerts an adverse effect such as salt damage, leaf scorch or the like. In the case of applying it through addition to hydroponic water, however, in order not to contaminate. and rot the hydroponic water, proline is, needless to say, preferably in the form free from impurities which cause such contamination and rot.

The withering-preventing and quick-acting nutrition supplementing agent for a plant such as a gramineous plant or the like of the present invention, containing proline as the effective ingredient, may be in the form suitable for applying it through soil or hydroponic water, where it is dissolved in an appropriate solvent such as water. In the case of foliar application, a solution form (a liquid preparation) having a proline concentration of 0.2 to 29 ppm is effective. Moreover, the agent may be formulated into powder, granules, or tablets by using an appropriate filler, binder or the like. In the case of dissolving with a solvent, the agent may be formulated by adding a fungicide, a surfactant, or a preservative from the viewpoint of prevention of rot. Furthermore, in the case of foliar application, concurrent use with a spreading/adhering a gent is effective.

With regard to suitable time for applying the withering-preventing and quick-acting nutrition supplementing agent of the present invention, in the case of lawn grasses, pasture plants and the like, application as an additional fertilizer, application after mowing grass, application at the beginning of withering or the like may be exemplified.

Examples of the fertilization method (the application method) include foliar application, soil application, and addition to hydroponic water. It is particularly effective to apply proline to the above-ground parts to be absorbed from the leaves of a plant such as a lawn grass, and inosine to the soil to be absorbed from the roots. In this case, the withering-preventing and quick-acting nutrition supplementing agent for a lawn grass is not in the form containing both proline and inosine together, but proline and inosine are each applied separately but at not so long interval to the above-ground parts and the soil, respectively.

As has been mentioned above, with regard to inosine, the present inventors have found that the combination of inosine and proline is remarkably effective as compared with other combinations of proline and a nucleoside other than inosine such as the combination of uridine and proline, the combination of adenosine and proline, and the like.

Foliar application of proline not only prevents withering of a plant such as a gramineous plant but also is effective as a means of feeding nitrogen immediately and promoting the growth (a quick-acting nutrition supplementing agent).

Application rate or amount varies depending on the time of application, the kind of gramineous plants (lawn grasses, rice plants, pasture plants, and the like), the cultivation density, the growing stage, and so on. In short, the rate can be determined as those values at which the prevention of withering and the growth of, e.g., a lawn grass cultivated by using the withering-preventing and quick-acting nutrition supplementing agent of the present invention are superior to those of the lawn grass cultivated under entirely the same conditions with the exception that the withering-preventing and quick-acting nutrition supplementing agent of the present invention has not been applied. It is possible to determine the value by preliminary comparative test easy to carry out for those skilled in the art. As has been mentioned above, in the case of foliar application, a solution having a proline concentration of 0.2 to 29 ppm is particularly effective and such a low concentration can be employed. That is, prevention of withering and promotion of growth of a gramineous plant can be effected at such a low concentration.

In addition, application rate of inosine can be from 0.05 to 1 ppm to the soil (5 to 100 g per 100 tons of soil) in the case of soil application, for example. In the case of hydroponic cultivation, inosine can be applied in an amount of 0.1 to 5 ppm to the hydroponic water.

EXAMPLE

The present invention will be described in greater detail below with reference to the example.

Example 1

(Hydroponic Cultivation of a Lawn Grass)

Seedlings of a lawn grass (European grass, evergreen lawn grass) were cultivated and divided into eight groups of A to H, one group being composed of 80 stocks. Then, they were cultivated hydroponically under the conditions shown in the following Table 1. In the groups B to H, inosine and uridine were added to each hydroponic liquid in such amount that the concentration became as shown in the table, and proline was diluted with water such that the concentration became as shown in the table and sprayed onto the leaves every day. Group A was the control.

On the 35th day, five average stocks which had not been withered were sampled from each group. As will be shown in the table, at the root, leaf length and total weight of the living plants, better growth was found in the proline-treated plot, especially at a concentration of 2 ppm. Furthermore, it was confirmed that the effect became more remarkable when 2 ppm of inosine was used in combination. In the table, the number of days till the plants were withered means the number of days from transplantation of the seedlings till about 70 percent of the leaves were withered.

Figure 2:
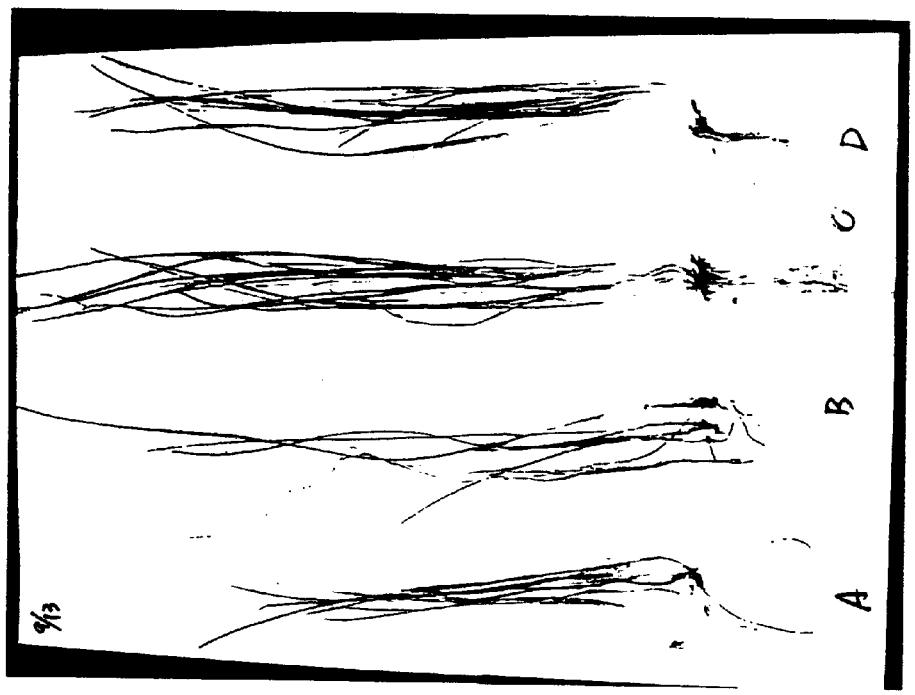
FIG. 2 shows the state of the grass plants after washed with water on the 35th day from the transplantation (Example 1).

For reference, photographs of the state of the pot cultivations of the groups A to D on the 35th day from the transplantation of the lawn grass plants are shown in FIG. 1. Furthermore, FIG. 2 shows photographs of the state of every five stocks of the same four groups on the 35th day from the transplantation of the grass plants. From these photographs, better growth was also found in the proline-treated plot, especially at a concentration of 2 ppm, and it was confirmed that the effect became more remarkable when 2 ppm of inosine was used in combination.

TABLE 1

| | Comparison of the lawn grass plants (5 stocks each) | | | | | |
|---|---|---|---|---|---|---|
| | Average root length | Leaf length (cm) | | Total weight of living | Number of days till the plants | |
| Group | (cm) | MIN. | MAX. | plant (g) | were withered | Remarks |
| A (Control) | 3 | 6 | 18 | 0.19 | 20 | Wilted and partially withered. |

TABLE 1-continued

Comparison of the lawn grass plants (5 stocks each)

| Group | Average root length (cm) | Leaf length (cm) MIN. | Leaf length (cm) MAX. | Total weight of living plant (g) | Number of days till the plants were withered | Remarks |
|---|---|---|---|---|---|---|
| B (2 ppm inosine) | 2 | 8 | 27 | 0.22 | 25 | Wilted and partially withered. |
| C (2 ppm inosine and 2 ppm proline) | 5 | 12 | 29 | 0.64 | 42 | Both leaves and stems were thicker than those in group D. |
| D (2 ppm proline) | 3 | 12 | 21 | 0.54 | 38 | Both leaves and steins were thick. |
| E (10 ppm inosine and 2 ppm proline) | 3 | 11 | 23 | 0.35 | 35 | Partially wilted. |
| F (35 ppm proline) | 2 | 8 | 20 | 0.28 | 28 | Partially wilted. |
| G (0.1 ppm proline) | 2 | 7 | 19 | 0.22 | 27 | Partially wilted. |
| H (2 ppm uridine and 2 ppm proline) | 2 | 7 | 23 | 0.23 | 27 | Partially wilted. |

[Effects of the Invention]

According to the present invention, application of proline or proline and inosine inhibits and prevents withering of a gramineous plant such as a lawn grass, and also affords nutrition effects easily.

What is claimed is:

1. A method for preventing withering and effecting nutritional supplementation of a gramineous plant, which comprises applying an effective amount of proline to said gramineous plant in need thereof.

2. The method of claim 1, wherein said gramineous plant is lawn grass.

3. The method of claim 2, wherein said lawn grass is a cold-district grass.

4. The method of claim 1, wherein said gramineous plant is rice.

5. The method of claim 2, wherein said lawn grass is on a baseball field.

6. The method of claim 1, wherein said composition is applied to soil.

7. The method of claim 1, wherein said composition is applied to hydroponic water.

8. The method of claim 1, wherein said composition is applied by foliar application.

9. The method of claim 2, wherein said lawn grass is on a golf course.

10. The method of claim 1, wherein said gramineous plant is a pasture plant.

11. A method for preventing withering and effecting nutritional supplementation of a gramineous plant, which comprises applying the composition comprising a liquid carrier and proline in an amount of from 0.2 to 29 ppm based on the total composition, to said gramineous plant in need thereof.

12. The method of claim 11, wherein said composition is applied to soil.

13. The method of claim 11, wherein said composition is applied to hydroponic water.

14. The method of claim 11, wherein said composition is applied by foliar application.

15. A method for preventing withering and effecting nutritional supplementation of a gramineous plant, which comprises performing foliar application of the composition comprising proline and another ingredient selected from the group consisting of inosine and serine, to said gramineous plant in need thereof.

16. The method of claim 15, wherein said composition is applied to soil.

17. The method of claim 15, wherein said composition is applied to hydroponic water.

18. The method of claim 15, wherein said composition is applied by foliar application.

19. The method of claim 1, wherein said composition is applied when said gramineous plant begins to wither.

20. The method of claim 2, wherein said composition is applied to said lawn grass after mowing.

21. The method of claim 2, wherein said composition is applied when said gramineous plant begins to wither.

22. The method of claim 2, wherein said gramineous plant is lawn grass.

23. The method of claim 22, wherein said composition is applied to said lawn grass after mowing.

24. The method of claim 15, wherein said gramineous plant is lawn grass.

25. The method of claim 24, wherein said composition is applied to said lawn grass after mowing.

* * * * *